United States Patent [19]

Adams

[11] Patent Number: 4,587,835
[45] Date of Patent: May 13, 1986

[54] LIGHT PIPE AND HEATER APPARATUS

[75] Inventor: Gary E. Adams, Danbury, Conn.

[73] Assignee: International Business Machines Corp., Armonk, N.Y.

[21] Appl. No.: 690,073

[22] Filed: Jan. 9, 1985

[51] Int. Cl.[4] ............................................. G01N 30/74
[52] U.S. Cl. ...................................... 73/23.1; 250/343
[58] Field of Search ................. 73/23.1; 250/343, 344, 250/345, 428, 429; 356/440

[56] References Cited

U.S. PATENT DOCUMENTS 4,420,690 12/1983 Kuehl ................................. 250/428
4,440,013 4/1984 Adams ................................ 73/23.1

Primary Examiner—Stephen A. Kreitman
Attorney, Agent, or Firm—Joseph A. Biela

[57] ABSTRACT

A GC/IR system for analyzing the constituents of a gas sample is disclosed and claimed in which a floating light pipe assembly is disposed in a bore and troughs of a heater chamber in a heater assembly. The floating light pipe assembly has two transfer tubes and a light pipe tube that provide a completely chemically resistant path to the flow of a gas sample and carrier gas from a GC capillary column to a supplemental GC detector. The flow path is chemically inert since no contaminating sealants are used and substantially all of the flow path is gold plated. The light pipe assembly "floats" because it is allowed to thermally expand within the heater chamber so that high reflectivity in the IR region will be maintained as the light pipe assembly is being heated by the heater plates on opposite sides of the heater chamber.

25 Claims, 8 Drawing Figures 4,587,835

LIGHT PIPE AND HEATER APPARATUS

BACKGROUND OF THE INVENTION

1. Field of the Invention

This invention relates to improvements in gas chromatograph (GC), Fourier transform (FT) infra-red (IR) spectroscopy systems and, more particularly, to improvements in a GC/IR interface assembly which can be used in substantially any commercial FTIR sample chamber.

2. Prior Art

The combination of GC and FTIR analytical techniques is well known whereby a sample gas is separated into its constituents. An FTIR spectroscope and data processing system detects and rapidly analyzes the constituents. GC/FTIR systems generally include a GC having an oven containing a separating column. A carrier gas continuously flows through the separating column. A sample gas mixture, initially in liquid form, is injected into the GC and vaporized so that its constituent parts are "picked up" by the carrier gas and separated as the carried constituents flow through the GC separating column. The column effluent enters a light pipe through which each constituent (or peak) moves at different times. IR light (energy), provided by an interferometer, is directed through one end of the light pipe and is absorbed by the constituent parts thereby identifying the type and quantity of each constituent. The IR energy is detected at the opposite end of the light pipe such that an electrical signal or interferogram is created. The interferogram then becomes input data to a data processing system. In the data processing system, the "digitized" interferogram is subjected to Fourier analysis as well as other mathematical computations that provide the characteristics of the constituents of the sample.

In prior art GC/FTIR systems, the separating column is located within an oven and the light pipe is located external to the oven. A transfer tube is connected, at one end, to the exit end of the separating column, and at the other end, to the input end of the light pipe. U.S. Pat. No. 4,440,013, assigned to the assignee of the present invention, shows how a narrow component peak from the GC separating column can be transferred to the input end of the light pipe in order to achieve high chromatographic resolution and a high signal-to-noise ratio when using the IR detector. However, the problem remains of transferring the sample to a GC detector which is connected, via a transfer tube, to the output end of the light pipe. The type of sealants and fittings used to connect the transfer tube to the output end of the light pipe detector as well as the type of transfer tube used can cause or be responsible for turbulence and eddy currents which create dead volumes such that peak (band) broadening and tailing of the sample can occur. Peak broadening will affect, by reducing, the chromatographic resolution and the spectrometric detection of the constituents. This problem becomes more acute if an air tight seal is not provided between the transfer tubing and the output end of the light pipe. The problem is further exacerbated if the sealants that are used contaminate or absorb the sample thereby creating a source of error.

Also, in prior art GC/FTIR systems, the light pipe extends through a heat transfer block around which is wrapped a heater coil. The transfer tube(s) also extend through a second heat transfer block which is wrapped by another heater coil. During operation of the system, the various heaters are independently energized in order, for example, to prevent condensation of gas in the light pipe. However, prior art heaters implemented in this manner do not permit optimal temperature control. Also, the prior art systems, having a variety of transfer tubes, fittings, heat transfer blocks and heater coils, are difficult to manufacture and to maintain. Furthermore, prior art light pipes, associated transfer tubing, heat transfer blocks and heater coils are not easily adapted to be received by and to work with a variety of different GC/FTIR systems.

U.S. Pat. No. 4,420,690 assigned to Bio-Rad Laboratories, Inc. discloses a sample cell which includes a small-bore hollow tube through which a gas stream flows and end windows at the ends of the tube which are captivated within a thermally conducting holder. The cell also includes matching bores in the holder for accommodating fluid transfer lines which are sealed to the tube. The windows are sealed to the ends of the tube by a sealant which is exposed to the flow stream thereby exposing the sample to contamination or reaction with the sealant. The sealant is also used to seal the transfer lines to the tube thereby again exposing the sample to contamination or reaction with the sealant. The windows are held at the ends of the tube with a sealant, an elastic ring such as a rubber spring and a washer. The washer is secured by screws.

Accordingly, it is an object of this invention to provide a compact, easily removable GC/IR interface accessory containing a floating light pipe assembly, heater block and mirrors for use in substantially any FTIR spectrometer sample chamber.

Another object of this invention is to reduce the peak broadening in the transfer tube at the output end of the light pipe in order to achieve high resolution in the GC detector.

Another object of the invention is to provide an airtight interface between the transfer tube and the output end of the light pipe.

A further object of the present invention is to simplify the attachment of the light pipe to the transfer tubes by substantially eliminating the use of sealants and by minimizing the number of fittings without affecting high chromatographic resolution and spectrometric detection due to interaction of the sample with the seals and fittings.

An object of the invention is to eliminate unswept areas or dead spaces in the flow path of the GC/IR interface assembly.

An object of the invention is to simplify the heating of the light pipe and transfer tubes while at the same time eliminating cold spots and facilitating the adaptation of the light pipe and transfer tubes for use in a variety of FTIR sample chambers.

Another object of the invention is to provide optimal temperature control of the light pipe and transfer tubes while at the same time facilitating the adaptation of the light pipe and transfer tubes for use in a variety of FTIR sample chambers.

A further object of the invention is to improve upon the chemical inertness of the fittings and transfer tubes in order to provide accurate sample detection.

SUMMARY OF THE INVENTION

A GC/IR system for analyzing the constituents of a gas sample is disclosed and claimed in which a floating light pipe assembly is disposed in a bore and troughs of a heater chamber in a heater assembly. The floating light pipe assembly includes two transfer tubes and a light pipe tube that provide a chemically inert flow path for transferring constituents of a gas sample from a GC capillary column to a supplemental GC detector. One transfer tube is connected to the GC capillary column while the other transfer tube is connected to the supplemental GC detector. The heater assembly minimizes the temperature drop of the gas sample as it passes through the floating light pipe assembly, in the heater assembly, at high velocity. The floating light pipe assembly also maintains high IR reflectivity in the IR region.

DESCRIPTION OF THE PREFERRED EMBODIMENTS

Figure 1A:
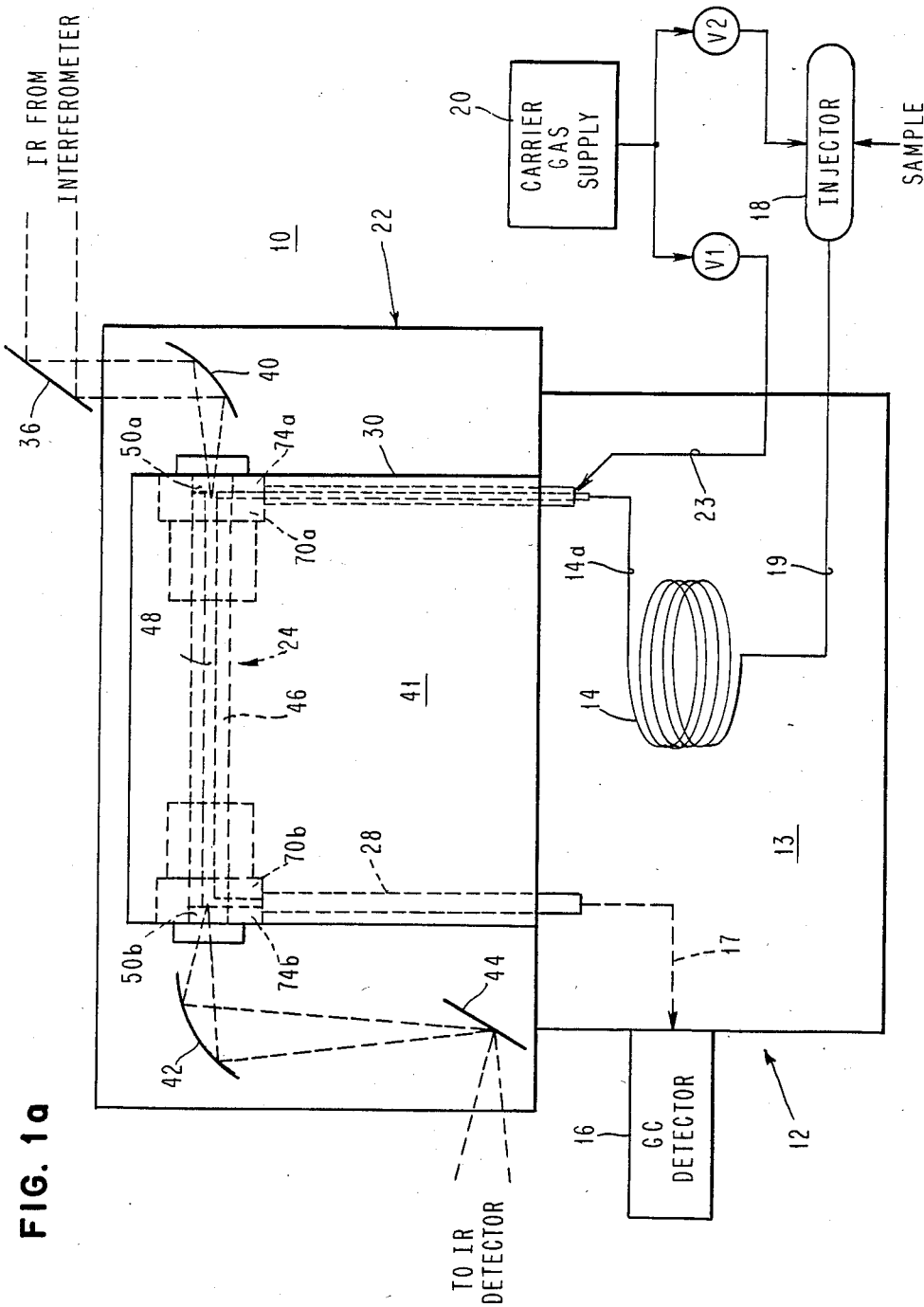
FIGS. 1a–1b are schematic diagrams of the GC/IR system.

FIG. 1a shows GC/FTIR system 10 embodying the invention. GC/FTIR system 10 includes GC 12, GC capillary column 14, GC detector 16, sample injector 18, carrier gas supply 20 and GC/IR interface accessory 22. The GC/FTIR system also includes a spectrometer (not shown) which can be one of the IR/90 or IR/80 series of FTIR spectrometers available from IBM Instruments, Inc. Such spectrometer was described in the above-cited U.S. Pat. No. 4,440,013.

GC/IR interface accessory 22, which is shown in FIGS. 1a through 1d, includes light pipe assembly 24 having first transfer tube means 26 and second transfer tube means 28 and heater assembly (chamber) 30. Heater chamber 30 is further enclosed by an insulator (not shown). The GC/IR interface accessory also includes such components as mirrors, e.g. 40 and 42, which are only shown in FIGS. 1a through 1d, metal fittings, 74a and 74b, flanges, 70a, 70b, 76a and 76b, O-rings, 72a–d, cover plates 30o and 30i and windows 50a and 50b. The components of GC/IR interface accessory 22 positioned within (or touching) heater chamber 30 are more clearly shown in FIG. 2. The heater assembly provides a unique heating chamber that eliminates "cold spots" in light pipe assembly 24. As can be seen in FIGS. 1a–d and 2, only one end of each transfer tube extends beyond an outer surface of the heater chamber (and insulator) to facilitate connection to transfer tubes 17 and 14a in oven 13 which lead to supplemental detection means, e.g. GC detector 16, and GC capillary column 14, respectively. Transfer tube 14a, which is an extension of GC capillary column 14, is the unique sample input transfer tube to light pipe assembly 24. The GC/IR interface accessory is compact and is easily inserted into (dropped into) any FTIR sample chamber. In other words, interface accessory 22 is mounted on removable (standard) sample chamber base plate 41 which permits the accessory to be "dropped in" to the sample chamber as one complete, ready-to-use compact unit. Transfer tubes 26 and 28 (flow paths) are glass-lined for chemical inertness. In fact, all components that are exposed to the gas (sample and carrier), except for windows 50a and 50b, are gold coated surfaces, or fused silica coated surfaces with separation media, e.g. inner tube 26i discussed below. In particular, metal fittings (described below) are gold plated, the ends of light pipe 46 are gold coated and internal surface 51 of light pipe 46 is gold coated. The fused silica coated surface with separation media is found in GC capillary column 14 which becomes the sample and carrier gas input transfer tube 26i discussed below. (Transfer tube means 28 may also include an (optional) inner output tube (not shown) which acts as a gas return transfer tube. This output tube would also have a fused silica coated surface. If this inner output tube were utilized, transfer tube means 28 would not have to be glass-lined for chemical inertness. In fact, transfer tube means 28 could then be unlined steel or copper or aluminum.)

The remaining components of the GC/FTIR system can best be described in terms of its operation. In an embodiment shown in FIG. 1a, an IR light source (not shown) directs IR energy from the interferometer to first mirror 36. Second reflecting mirror 40 receives the energy reflected by first reflecting mirror 36, and focuses and directs the IR energy into one end of light pipe tube 46. The energy emerging from light pipe tube 46 is reflected and directed by third and fourth mirrors, 42 and 44 respectively, into an IR detector (not shown). Reflecting mirrors 40 and 42 are moveably positioned off-axis with respect to opposite ends of the light pipe in order to better control the axis of the IR (light) beam so as to (optimally) utilize (reflect) more IR energy.

Figure 1B:
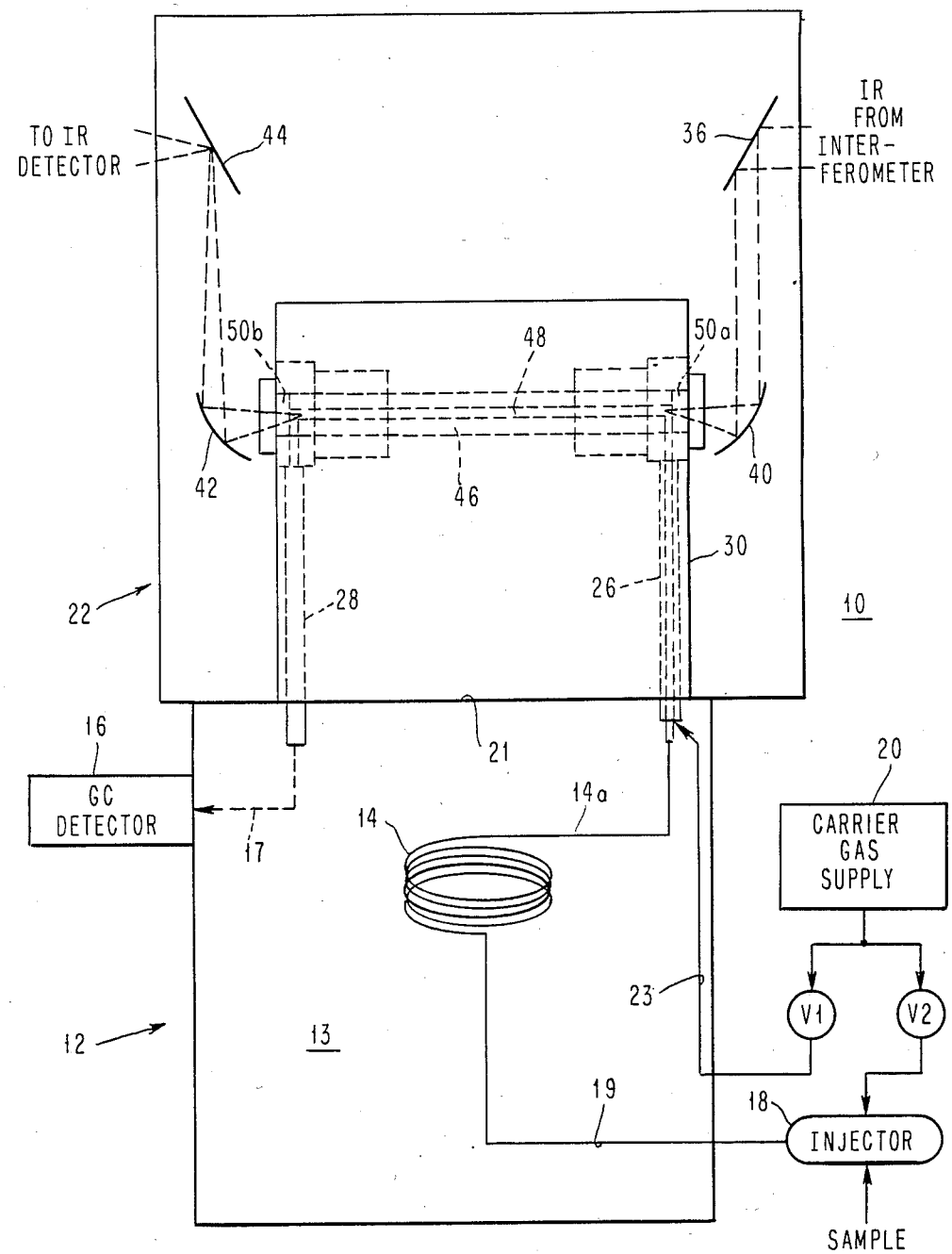

In FIG. 1b, another embodiment of the GC/IR interface accessory is shown with the light pipe assembly enclosed by the heater assembly (and insulator) in the manner described herein. However, in this embodiment, the GC/IR accessory further includes first mirror 36, which was discussed above and shown in FIG. 1a as being separate from the interface accessory. In FIG. 1b, all of the mirrors are included as part of the compact, drop-in GC/IR accessory mounted on base plate 41. Each component shown in FIG. 1b is substantially the same as shown in FIG. 1a and described above. The difference is that the drop-in accessory now includes each of the four mirrors.

Figure 1C:
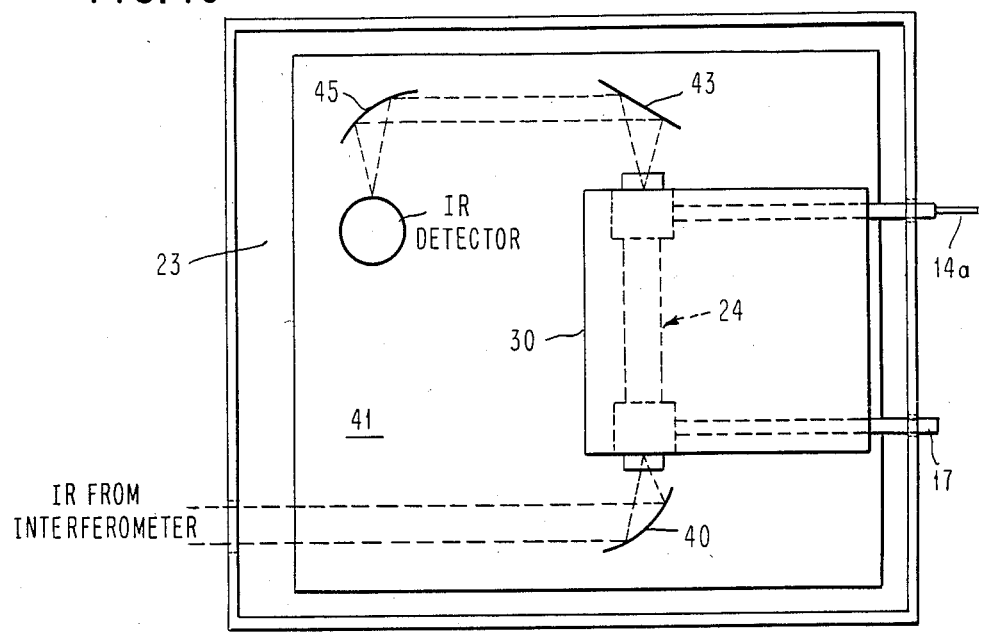
FIGS. 1c–1d are schematic diagrams of the GC/IR interface accessory in a sample chamber of a GC/IR system.

In FIG. 1c, heater chamber 30 (with light pipe assembly 24) is shown mounted on base plate 41. Colimated light is reflected off first mirror 40 and directed through the light pipe tube of light pipe assembly 24. Light emerging from the light pipe tube is reflected by second mirror 43 to third mirror 45. The light is then reflected by mirror 45 and directed into an IR detector which is also mounted on base plate 41. The mirrors 40, 43 and 45, heater chamber 30 and IR detector are all mounted on base plate 41 which is then "dropped in" to sample chamber 23.

Figure 1D:
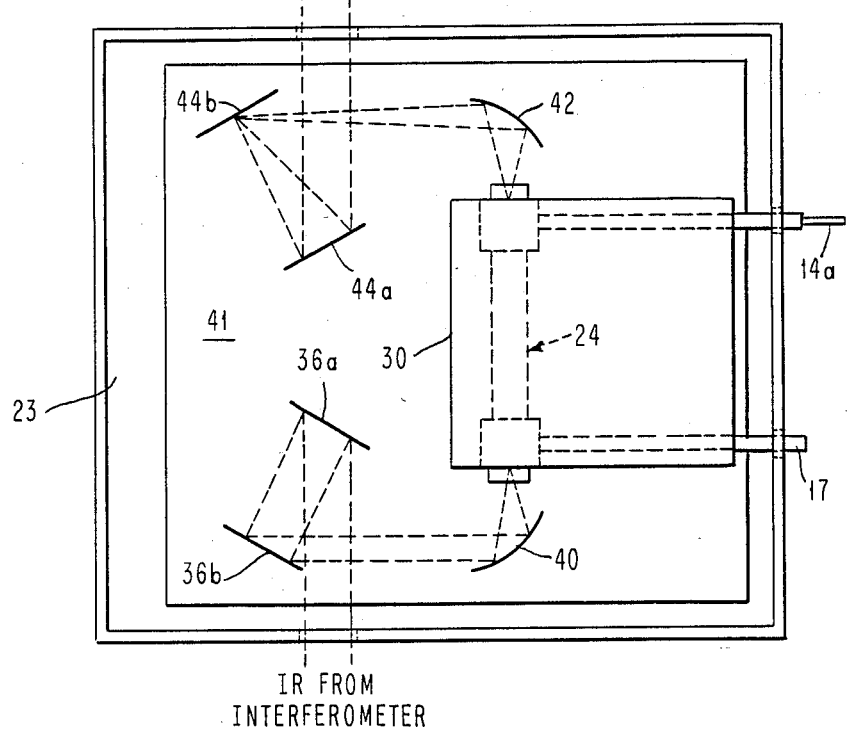

In FIG. 1d, several additional mirrors have been added (mounted on base plate 41). The IR detector is not mounted on the base plate but is external to sample chamber 23. Light from the interferometer is first reflected from mirror 36a to mirror 36b and then to off-axis mirror 40. The light is reflected off mirror 40 and directed into the light pipe tube of light pipe assembly 24 which is in contact with heater chamber 30. The light energy emerging from the light pipe tube is reflected by off-axis mirror 42, then by mirrors 44b and 44a. Mirror 44a directs the reflected light to an external IR detector. (Oven 13 is not shown in FIGS. 1c and 1d.)

Referring to FIGS. 2, 3, 4a and 4b, light pipe assembly 24 includes glass or, preferably, fused silica light pipe (tube) 46 having internal surface 51, forming central bore (or flow path) 48, which is coated with a reflective coating such as gold. Tube 46 is intended to propagate radiant IR energy (as well as to allow gas to flow) through bore 48. Gold coating is used as a reflective coating in the bore in order to produce high reflectivity in the IR region and to be non-reactive to the sample, i.e. to increase chemical inertness. (Gold coating is also applied at the ends of tube 46, except for the surface of the windows, and on all metal fittings to provide for chemical inertness.) First window 50a, transparent to IR energy, has a flat surface normal to the longitudinal axis of and in compressive, air-tight contact with one end (the input end) of tube 46 for the purpose of closing off one end of bore 48 in order to cause the gas (sample and carrier) admitted to the input end of the light pipe, within close proximity to the first flat-surface window, to flow through bore 48. Second window 50b has a flat surface normal to the longitudinal axis of and in compressive, air-tight contact with the other end (the output end) of tube 46 for the purpose of closing off the other end of bore 48 in order to cause the sample and carrier gas to flow from bore 48 through second (output or return) transfer tube means 28.

Figure 2:
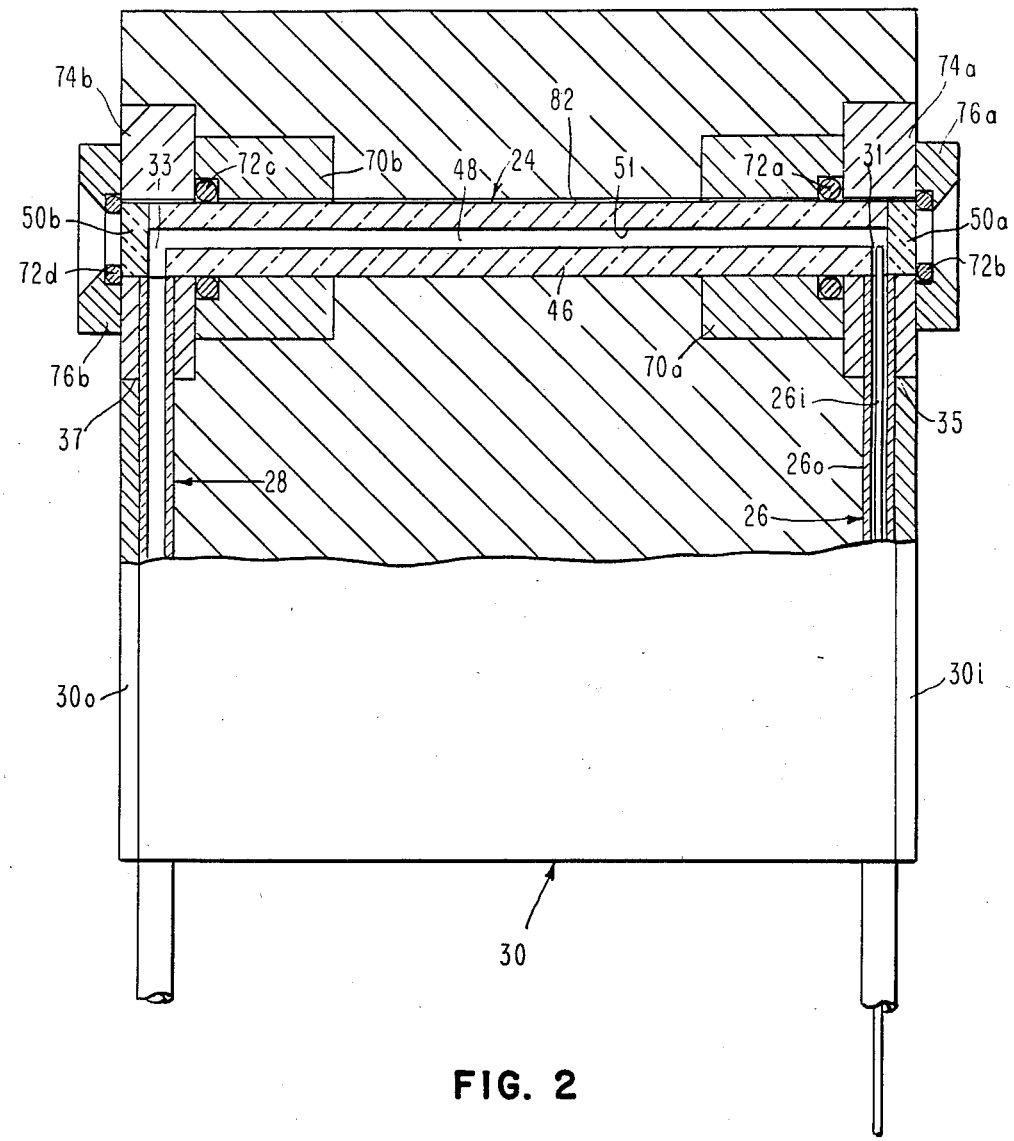
FIG. 2 is a cross-sectional frontal view of the heater assembly and light pipe assembly of the GC/IR interface accessory.

First (input) transfer tube means 26 includes coaxial (concentric) outer tube 26o and polyimide-coated fused silica inner tube 26i. As is shown in FIG. 2, the outer surface at one end of outer tube 26o comes in contact with and is secured to the surface of a passageway in first metal fitting 74a by brazing, soldering or welding. Outer tube 26o as well as metal fitting 74a are then gold plated to provide for chemical inertness. The interior passageway of outer tube 26o communicates with bore 48 via first groove 31 formed in the input end of tube 46 (as discussed below) to provide for the flow of auxiliary carrier gas from carrier gas supply 20 to bore 48. The end of tube 46 has formed along its radius groove 31 for providing a flow path between first transfer tube means 26 and bore 48 in light pipe tube 46. Outer tube 26o abuts the side of the light pipe tube and the side of the first window as shown in FIG. 2. As shown in FIGS. 1a and 1b, carrier gas is provided through valve V1, along line 23, through the interior passageway of outer tube 26o and into bore 48 via first groove 31. Effluent sample gas (mixture) emerging from polyimide-coated fused silica inner tube 26i, which extends through first groove 31, discharges directly into bore 48 (within close proximity to a flat surface of first window 50a) into the path of IR energy being transmitted through bore 48 substantially as described above with respect to FIGS. 1a through 1d. The sample gas (carried by carrier gas provided through valve V2) is injected into the GC capillary (separation) column 14 by injector 18, via line 19, and passes through the passageway of inner tube 26i into bore 48. The circumference of the interior passageway of outer tube 26o is substantially aligned with the circumference of first groove 31 which extends radially outward from bore 48 in tube 46 within close proximity to first window 50a. The end of outer tube 26o which abuts the side of light pipe tube 46 and the side of first window 50a is sealed to the surface of the passageway in first fitting 74a with metallic brazing, solder, or welding. Tube 26o is only fitted snuggly against the sides of the light pipe tube and the first window but is not sealed to either the light pipe tube or first window. (Since inner tube 26i is implemented in this embodiment, outer tube 26i could be unlined steel or copper or aluminum rather than glass-lined steel. Polyimide-coated fused silica inner tube 26i is not sealed to any portion of light pipe assembly 24 in the region near first window 50a.)

Second (output) transfer tube 28 is, in this case, also made of glass-lined steel tubing, in order for the constituent peaks, obtained from separation column 14, to be retained as the gas sample is conveyed from inner tube 26i, through light pipe tube 46, to GC detector 16. In other words, the effluent sample gas from the separation column flows to GC detector 16 with virtually no band broadening through the light pipe assembly. In order to retain the original chromatographic peak shapes, the outer surface at one end of transfer tube means 28 is tightly secured to the surface of a passageway in second metal fitting 74b by brazing, soldering, or welding. Transfer tube means 28 as well as metal fitting 74b are then gold plated to provide for chemical inertness. The interior passageway of second transfer tube means 28 communicates with bore 48 via second groove 33 formed in the output end of tube 46 (as discussed below) to provide for the flow of the sample and carrier gas from light pipe tube 46 to GC detector 16. Transfer tube means 28 abuts the side of the light pipe tube and the side of the second window as shown in FIG. 2. The circumference of the interior passageway of transfer tube means 28 is substantially aligned with the circumference of radial second groove 33. (If an optional polyimide-coated fused silica inner output tube is inserted into transfer tube means 28, the end of the inner output tube would be sealed at the end of transfer tube means 28, in the region of groove 33, with ceramic sealants, fused salts, silicon, graphite, or polymer (elastomer) materials.)

Disposed at the end of tube 46 are radial grooves 31 and 33 as indicated above. Radial groove 31 has substantially the same diameter as the interior passageway of outer tube 26o of first transfer tube means 26 while radial groove 33 has substantially the same diameter as the interior passageway of second transfer tube means 28. Such radial grooves can be formed at each end of light pipe tube 46 by suitable glass working techniques, e.g. grinding. Once grooves 31 and 33 are formed at the end of light pipe tube 46, the ends of tube 46 are coated with gold.

Figure 3:
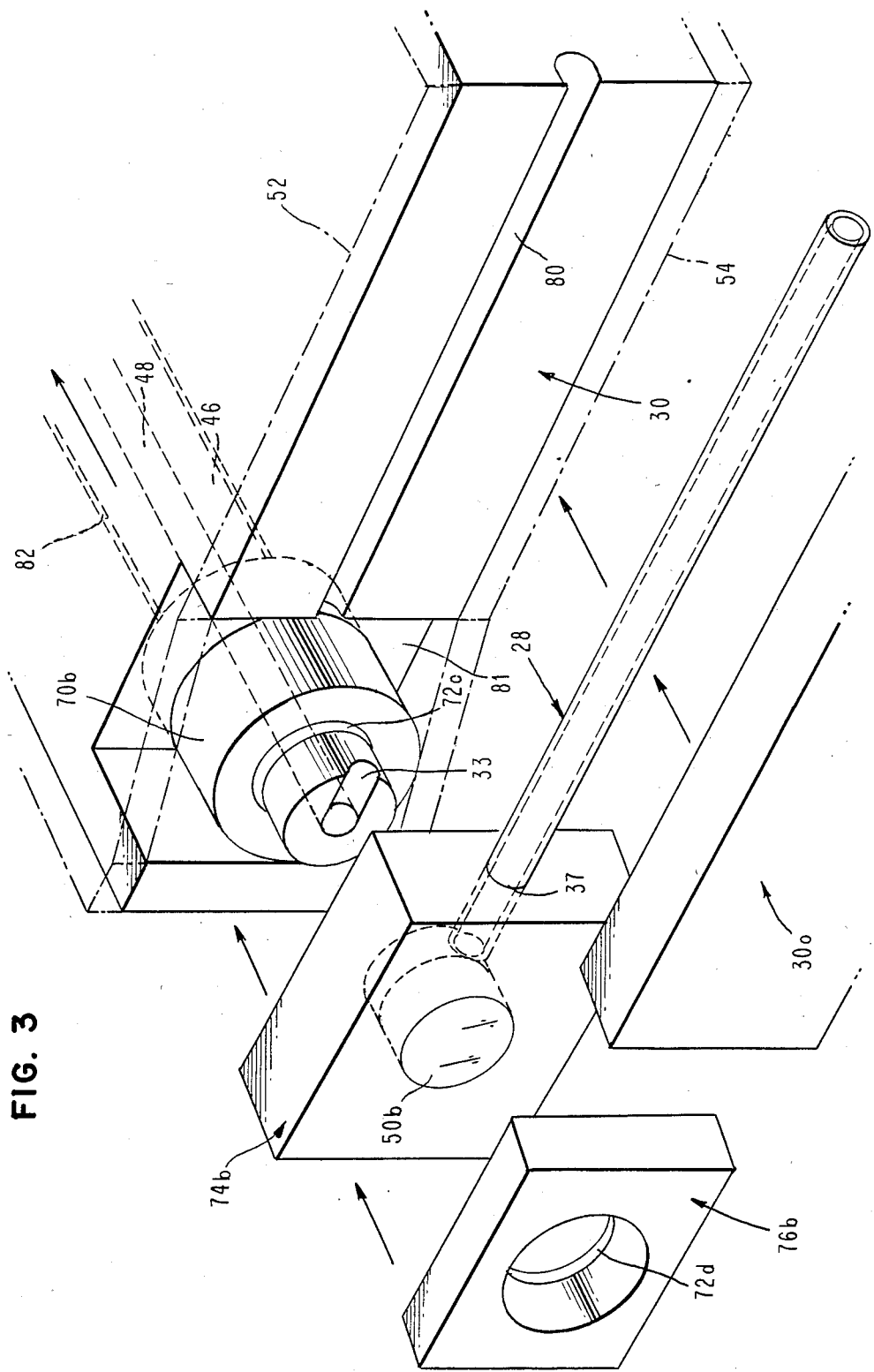
FIG. 3 is a cross-sectional perspective side view of the heater assembly and light pipe assembly of the GC/IR interface accessory.

As shown in FIGS. 2 and 3, heater chamber 30 includes a heat sink block (a substantially solid plate). The heat sink block is sufficiently thick so as to permit cavities properly positioned therein to receive the light pipe assembly when portions of the light pipe assembly come into contact with the heater chamber. The heater chamber is substantially enclosed by an insulator. The heater chamber is part of a heater assembly which includes two flat plate heating elements (52 and 54) on opposite sides of heater chamber 30 and cover plates (30o and 30i). The flat plate heating elements provide improved heat transfer characteristics and temperature control over prior art devices, especially those which implement heating coils. Flat plate heaters are also easier to maintain and are easily adapted to be received by a variety of different FTIR systems. The heater plates are bolted to their respective sides of the heat sink block. The heater plates provide a simplified way of heating the light pipe assembly.

Heater chamber 30, partially shown in FIG. 3, has a bore and troughs therethrough and therein which receive light pipe assembly 24. In particular, the solid heat sink block of heater chamber 30 includes second open-ended trough 80 adapted to loosely receive a lengthwise portion of second transfer tube means 28. The second trough is on and substantially parallel to the length-wise edge of a first side of the solid heat sink block. A first open-ended trough (not shown) for (loosely) receiving a length-wise portion of first transfer tube means 26 runs substantially parallel to the second trough, but on a second side of the block opposite the first side. The heat sink block further includes open-ended bore 82 which is substantially parallel to another side of the heat sink block, but substantially perpendicular to the first and second troughs. A first (output) end of bore 82 opens out on the first side of the block into first recess 81 which has length and width dimensions slightly larger than the diameter of the circular (output) end of bore 82. A second (input) end (not shown) of bore 82 opens out on the second side of the block into a second recess (not shown) which has dimensions substantially equivalent to the dimensions of first recess 81, but on a side of the heat sink block opposite thereto. FIG. 3 shows flange 70b, as well as light pipe tube 46, sliding into position in bore 82. FIG. 2 shows the flange and the light pipe tube properly positioned in bore 82.

Figure 4A:
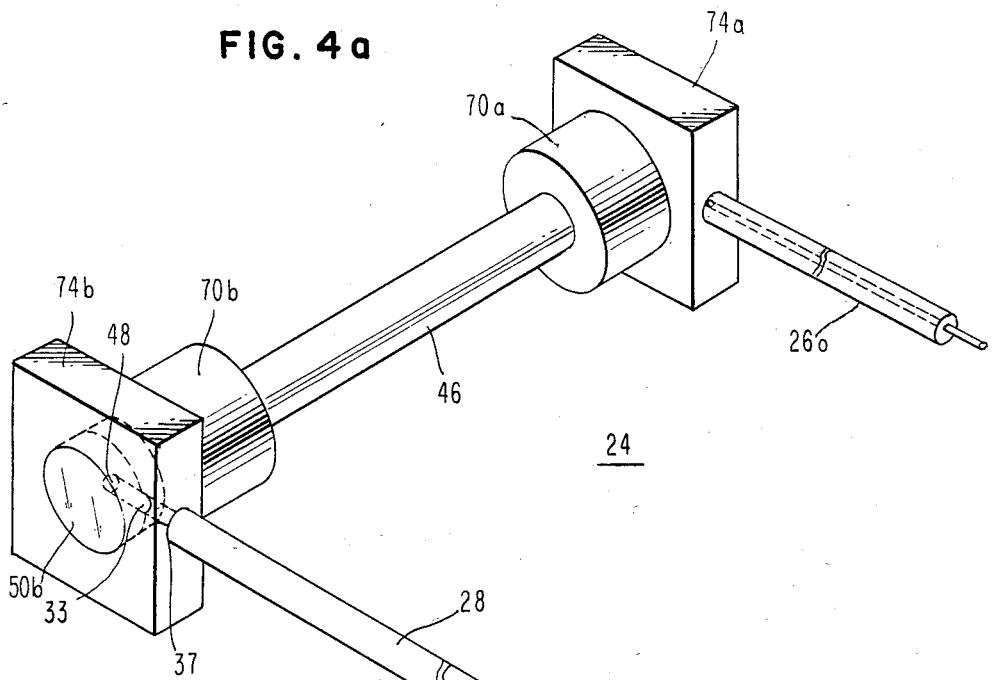
FIG. 4a–4b are perspective views of the light pipe assembly of the GC/IR interface accessory showing schematically a portion of the flow path.
Figure 4B:
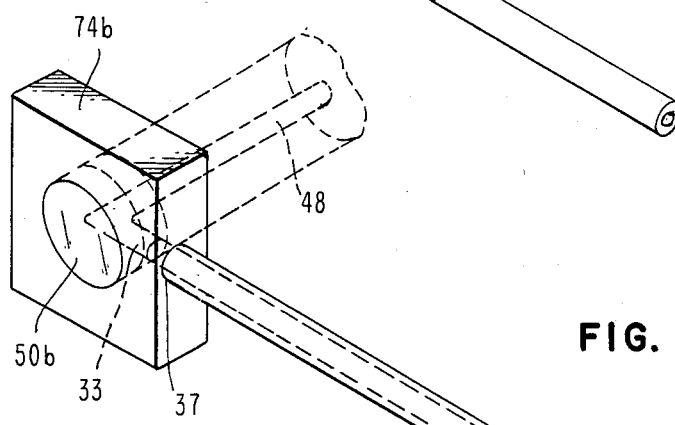

Tube 46 of light pipe assembly 24 is adapted to receive about its circumference first and second compression flanges 70a and 70b as shown in FIGS. 4a–b. In particular, once light pipe tube 46 slides into bore 82, flange 70b slides, like a ring, about tube 46 near its output end and flange 70a slides, like a ring, about tube 46 near its input end. Bore 82 is sufficiently large at its extreme ends in the heater chamber to receive first and second flanges 70a and 70b when tube 46 is positioned in the bore of the heat sink block of heater chamber 30. As shown in FIGS. 2 and 3, the extreme ends of tube 46 extend beyond the compression flanges such that the extreme output end of the tube extends out into first recess 81 and the extreme input end of the tube extends out into the second recess once the tube has been properly positioned in bore 82. Second trough 80 is adapted to receive a lengthwise portion of second (output) transfer tube means 28 such that the transfer tube means comes into contact with the heat sink block of heater chamber 30. The first trough is likewise adapted to receive a lengthwise portion of first (input) transfer tube means 26 such that outer tube 26o comes into direct contact with the heat sink block of heater chamber 30. Once the input and output transfer tube means are received by their respective troughs on opposite sides of the block, cover plates 30o and 30i are positioned over and cover the otherwise exposed lengthwise portions of the transfer tubes. In particular, first cover plate 30o covers the exposed lengthwise portion of transfer tube 28. Second cover plate 30i covers the exposed lengthwise portion of transfer tube 26. The cover plates are then fastened, e.g. bolted, to the sides of the heat sink block. As a result, substantially all of the gas-swept components of light pipe assembly 24 are in contact with the heat sink block so that the heater chamber can provide optimal temperature control of the contents of light pipe assembly 24. There is sufficient space in each of the troughs so as to accomodate (slight) movement in substantially any direction by the transfer tube means. The transfer tube means can be said to "float" in the troughs. It is understood that the troughs can be any shape, e.g. circular, V-shaped, etc.

Light pipe tube 46 is tightly fitted between first and second windows 50a and 50b wherein each window is received by an aperture in, and supported by, a metal fitting. As shown in FIGS. 4a–b, second fitting 74b includes several apertures therein and therethrough one of which is adapted to receive and retain window 50b and another of which is adapted to receive an end of (output) transfer tube means 28 such that effluent sample gas can discharge directly into transfer tube means 28 from bore 48 via groove 33. The central axis of each aperture in one fitting are substantially perpendicular to each other and lie substantially in the same plane. Specifically, the apertures in each fitting form "T" shaped passageways within each fitting. Transfer tube means 28 is tightly secured and sealed, at brazed joint 37, to second fitting 74b. Once the transfer tube is brazed, the fitting and transfer tube means are gold plated to provide a chemically inert flow path to gas flowing through the fitting. First fitting 74a also includes several apertures therein and therethrough one of which is adapted to receive and retain window 50a and another of which is adapted to receive an end of (input) transfer tube means 26 such that sample gas (and carrier gas) discharge directly into bore 48 from transfer tubes 26i and 26o via groove 31. Transfer tube means 26, i.e. outer tube 26o, is tightly secured and sealed at a brazed joint in first fitting 74a. Once the transfer tube is brazed, the fitting and transfer tube means are gold plated to provide a chemically inert flow path to gas flowing through the fitting. The aperture in second fitting 74b that receives window 50b also receives the extreme output end of light pipe tube 46 such that one flat (inner) surface of window 50b blocks off one end of bore 48 forcing gas flow to occur through second groove 33 from bore 48 to transfer tube means 28. In other words, the output end of light pipe tube 46 is in air-tight contact with one flat (inner) surface of window 50b in order to create a flow path from bore 48 to transfer means tube 28 via groove 33. Likewise, the aperture in first fitting 74a that receives window 50a also receives the extreme input end of light pipe tube 46 such that one flat (inner) surface of window 50a blocks off the other end of bore 48 forcing gas flow to occur through first groove 31 from transfer tube means 26 to bore 48. In other words, the input end of light pipe tube 46 is in air-tight contact with one flat (inner) surface of window 50a in order to create a flow path from transfer tube means 26 to bore 48 via groove 31.

High temperature first (sealing) O-ring 72a is retained between first compression flange 70a and first fitting 74a and acts as a seal around the circumference of tube 46. First fitting 74a is fastened, e.g. bolted, to first compression flange 70a. High temperature second O-ring 72b is retained between first fitting 74a and first window retaining flange 76a (and first window 50a) within close proximity to (touching) the edge of a flat (outer) surface of first window 50a. First window retaining flange 76a is fastened, e.g. bolted, to the end of first fitting 74a for compressively holding the first window firmly in place against one (input) end of tube 46. Second (sealing) O-ring 72b is used to prevent gas from escaping around the edges of the first window as well as to keep the inner surface of the first window firmly in contact with the input end of tube 46 in order to provide for gas flow to occur from transfer tube means 26 to bore 48 via groove 31. High temperature third O-ring 72c is retained between second compression flange 70b and second fitting 74b and acts as a seal around the circumference of tube 46. Second fitting 74b is fastened, e.g. bolted, to second compression flange 70b. High temperature fourth O-ring 72d is retained between second fitting 74b and second window retaining flange 76b (and second window 50b) within close proximity to (touching) the edge of a flat (outer) surface of second window 50b. Second window retaining flange 76b is fastened, e.g. bolted, to the end of second fitting 74b for compressively holding the second window in place against the other (output) end of tube 46. Fourth (sealing) O-ring 72d is used to prevent gas from escaping around the edges of the second window as well as to keep the inner surface of the second window firmly in contact with the output end of tube 46 in order to provide for gas flow to occur from bore 48 to transfer tube means 28 via groove 33. The windows are fabricated of a material chosen to be highly transmissive in the IR region and to be non-reactive to the sample gas. Typically, windows are made of salts, glass, fused silica or other optically transmissive materials known in the art. Each O-ring is made of fluid-impervious, chemically inert, nonleachable material. The O-rings may be made of rubber, a perfluoro elastomer, graphite or a soft metal seal. (An elastomer can outgas at higher temperatures.) The windows, fittings, window retaining flanges, compression flanges, tube 46 and transfer tube means 26 and 28 (GC/FTIR system components) are all easily removable for maintenance purposes. The components described herein facilitate construction, provide greater reliability over the closest known art and improve serviceability. They are not permanent (fixed) features.

GC 12 includes oven 13 in which is located continuous, one-piece, flexible narrow bore capillary (separation) column 14 of polyimide-coated fused silica. One end of the column is connected to injector 18 by line 19. The injector receives a (gas) sample and carrier gas from supply 20. Valve V2 permits the flow rate of the carrier gas to be adjusted or regulated. The other end (transfer line 14a) of (separation) column 14 passes through the glass-lined interior of outer tube 26o and becomes inner tube 26i. The effluent from the inner tube is admitted to bore 48 in light pipe assembly 24. A valve V1 is connected between supply 20 and line 23 for controlling the flow of an auxiliary supply of a carrier gas through the interior passageway of outer tube 26o about the exterior of inner tube 26i. Another transfer line 17 receives gas passing from the light pipe assembly and directs it into GC detector 16 so that this detector can be used, in addition to the IR detector, to analyze the characteristics of the sample. (The polyimide-coated fused silica separation column, which becomes inner tube 26i that is inserted in outer tube 26o, can be coated with a bonded chromatographic coating to provide for chemical inertness. Such coating can be a high-temperature silicone or polymer coating.)

GC/IR interface accessory 22 may or may not be brought into contact with surface 21 of oven 13. However, in either case, an end of first and second transfer tube means, 26 and 28, penetrate the wall of oven 13 (below surface 21 as shown in FIGS. 1a-b) in order to receive and removably connect with transfer line 14a (which becomes inner tube 26i within the interior passageway of outer tube 26o) and transfer line 17, respectively, within the oven. The transfer lines (14a and 17) then become external to the oven only when entering heater chamber 30. (Copper or a thermally conducting material can be placed around transfer lines external to the oven and between the oven and heater chamber 30.) Therefore, this heating technique, which includes flat heating plates on each side of a heat sink block along with the high linear velocity of the sample and carrier gas through the light pipe assembly within the heater assembly, tends to minimize any temperature drop of the sample and carrier gas, while passing through the heater chamber, and to eliminate cold spots.

During operation of the FTIR system, heating elements 52 and 54 (as shown in FIG. 3) are energized to bring the desired operating parts of GC/IR interface accessory 22 to the proper temperature. In other words, the temperature in light pipe assembly 24 must be sufficiently high to prevent the condensation of any gas therein. When a sample is received from injector 18, it is vaporized and mixes with and is propelled through the system by the carrier gas, e.g. helium, nitrogen, argon, which has a flow rate controlled by valve V2. As the sample in the carrier gas passes through GC capillary column 14, the sample is separated into its constituents (peaks) by a well known partitioning process. The various constituents of the sample traveling through the column at different rates, as a result of differing physical properties, are absorbed to the stationary phase of the column's wall. The flow rate of the auxiliary carrier gas provided through line 23 to the interior passageway of outer tube 26o is controlled by valve V1 so that the auxiliary carrier gas can push each constituent (of the sample) as each flows from capillary column 14 through inner tube 26i and, subsequently, through bore 48 of the light pipe as a "slug". Each slug, in highly concentrated form, provides a high signal-to-noise ratio in the energy detected by the IR detector. Spectrometric analysis is performed by detecting the attenuation of a beam of the IR (light) energy passed through the sample in the light pipe. It is critical to the successful operation of the system that the axis of the light beam be controlled (variable) so as to obtain the optimal amount of light energy incident to the input end, i.e. through first window 50a, of the light pipe tube when spectrometric analysis is being performed on a sample. (As discussed above, mirrors are moveable and positioned off-axis so that an optimal amount of light energy is utilized.) The constituents flow through light pipe tube 46, and then through second transfer tube means 28 to GC detector 16, via line 17, for further analysis. Due to the attachment of the second transfer tube means to the light pipe and to the elimination of dead spaces, the further analysis is very accurate since peak broadening and tailing at the output end of the light pipe is significantly reduced.

The compact GC/IR interface accessory described herein can be readily disassembled and each component, i.e. of light pipe assembly 24, is easily serviceable and replaceable once first and second cover plates 30o and 30i and first and second window retaining flanges 76a and 76b are removed from the heater block. The cover plates and retaining flanges are easily, removably fastened to the heater block by screws, nuts and bolts and the like. The only material (other than the material used for the interior of tube means 26 and 28 and portions of windows 50a and 50b) to which the flow stream, i.e. sample and carrier gas, is exposed, as it flows from separating column 14 through light pipe assembly 24 to GC detector 16, is pure gold. In particular, the ends of first and second transfer tube means, 26 and 28, are metal brazed into fittings 74a and 74b respectively, and the whole of each metal fitting, both inside and outside, is gold plated. The ends of light pipe tube 46 as well as surface 51 of bore 48 are also coated with pure gold. The gold provides for an inert, chemically resistant flow path for the gas sample. First flat window 50a tightly abuts one end of tube 46 preventing gas (other than a negligible amount) from escaping at that end. Second flat window 50b tightly abuts the other end of tube 46 preventing gas (other than a negligible amount) from escaping at that other end. O-rings 72b and 72d are not in direct contact with the gas stream and, in fact, are outside the outer diameter of tube 46. The negligible amount of gas that might escape between each window-light pipe interface will be trapped by second and fourth sealing O-rings 72b and 72d. In other words, the number of GC/IR interface components, described in the prior art, have been reduced in order to minimize the number of locations in the flow path at which the sample is exposed to "contaminating material". This has not reduced chromatographic resolution and spectrometric detection. The other advantages of reducing the number of components are to facilitate manufacture and maintenance of the GC/IR interface accessory and to better preserve the shapes of the peaks presented to a supplemental detection means, i.e. GC detector 16. The improved gas flow path provides no areas unswept by sample gas such that the flow path is free from "dead spaces". That is, there are no regions in the flow path where gas can accumulate even for short periods of time. The velocity of gas flow through the light pipe is substantially uniform. The flow path is continuous and not interrupted.

The coefficients of thermal expansion of the light pipe assembly and the heater subassemblies are not substantially equal. It is unnecessary to try to match the thermal expansion properties of the light pipe assembly and heat sink block because the whole light pipe assembly 24 is free to float within the troughs and bore of heater chamber 30. In other words, there is space between the light pipe assembly and the heat sink block to allow for thermal expansion (and movement) of the light pipe assembly as it is heated so that high reflectivity in the IR region will be maintained. Therefore, light pipe assembly 24 can expand or contract (radially and longitudinally) independent of the heater chamber 30. This construction of the accessory allows for differences in thermal expansion between the heater block and the light pipe assembly. Otherwise, without a "floating" light pipe assembly, the light pipe tube 46, when heat ed, will distort or twist causing similar distortions in the gold inner surface 51 of tube 46 such that low (reduced) reflectivity in the IR region would occur.

Based on the previous discussion, it is understood that first transfer tube means 26, i.e. outer tube 26o, and second transfer tube 28 are glass-lined whenever polyimide-coated fused silica tubing is not inserted in either transfer tube means. This will be the case when a packed column GC system is used. The glass lining provides for a chemically inert (resistant) transfer system in the case when polyimide-coated fused silica tubing is not used in the transfer tube means. However, in the present case, both transfer tube means are glass-lined even though polyimide-coated fused silica tubing, e.g. inner tube 26i, is inserted in one of them, i.e. outer tube 26o. It is understood that since fused silica tubing is inserted in outer tube 26o, that outer tube 26o does not have to be glass-lined, i.e. chemically resistant.

Also, as a result of the above discussion, it is understood that gas, flowing through the light pipe assembly, does not come in contact with any sealants that may contaminate the gas sample. The flow path for the gas is completely, chemically inert since all metal fittings, portions of transfer tube means and the surface of light pipe tube bore are gold plated.

While the invention has been particularly shown and described with reference to perferred embodiments thereof, it will be understood by those skilled in the art that the foregoing and other changes in form and details may be made therein without departing from the spirit and scope of the invention.

What is claimed is:

1. In a GC/IR system for analyzing the constituents of a gas sample including an IR spectrometer for providing IR energy through a passageway in a light pipe tube, a GC capillary column for separating a sample into constituents, and a supplemental detection means and a carrier gas provided by a carrier gas input means, the combination comprising:
   a heater assembly including a heater chamber having a first and second trough therein and a bore therethrough, and
   a floating light pipe assembly including said light pipe tube removably disposed in said bore and first and second transfer tube means removably disposed in said first and second troughs for providing a chemically inert flow path for transferring said constituents of a gas sample from said GC capillary column, which is removably connected to said first transfer tube means, to said supplemental detection means, which is removably connected to said second transfer tube means, whereby said heater assembly in combination with the high velocity of said sample in said light pipe assembly minimizes the temperature drop of said gas sample while passing through said floating light pipe assembly which maintains high reflectivity in the IR region.

2. The GC/IR system of claim 1 in which said floating light pipe assembly is free to thermally expand while maintaining high reflectivity in the IR region.

3. The GC/IR system of claim 1 in which said flow path in said light pipe assembly is free from dead space thereby minimizing band broadening of said high velocity gas sample as said constituents of said gas sample are transferred from said GC capillary column to said supplemental detection means.

4. The GC/IR system of claim 3 in which said first transfer tube means includes an outer tube which abuts the side of said light pipe tube near a first end of said light pipe tube and to a first window which has a flat surface that abuts said first end of said light pipe tube for providing a continuous, non-interrupted flow path for transferring said constituents of said gas sample and said carrier gas from said first transfer tube means to said passageway in said light pipe tube at a substantially uniform velocity.

5. The GC/IR system of claim 3 in which said second transfer tube means abuts the side of said light pipe tube near a second end of said light pipe tube and to the side of a second window which has a flat surface that abuts said second end of said light pipe tube for providing a continuous, non-interrupted flow path for transferring said constituents of said sample and said carrier gas from said passageway in said light pipe tube to said second transfer means tube at a substantially uniform velocity.

6. The GC/IR system of claim 2 in which said heater assembly is heated by flat heater plates connected to opposite sides of said heater chamber.

7. The GC/IR system of claim 4 in which said first end of said light pipe tube has a groove therein through which said gas sample and said carrier gas are transferred from said first transfer tube means between said first window and said first end of said light pipe tube to said light pipe tube.

8. The GC/IR system of claim 5 in which said second end of said light pipe tube has a groove therein through which said gas sample and said carrier gas are transferred from said light pipe tube between said second window and said second end of said light pipe tube to said second transfer tube means.

9. The GC/IR system of claims 7 or 8 in which said light pipe tube is retained in said bore between said first and second windows which are compressively held against said first and second ends of said light pipe tube by first and second window retaining flanges.

10. The GC/IR system of claim 9 in which said first window is compressed between said first end of said light pipe tube and a first O-ring which is retained between said first window and said first window retaining flange, and said second window is compressed between said second end of said light pipe tube and a second O-ring which is retained between said second window and said second window retaining flange.

11. The GC/IR system of claim 10 in which said first window retaining flange is secured to a first fitting for compressively holding said first window against said first end of said light pipe tube, and said second window retaining flange is secured to a second fitting for compressively holding said second window against said second end of said light pipe tube such that said constituents of said gas sample come into contact with substantially only said light pipe tube, said first and second windows and said first and second transfer tube means as said gas sample is transferred from said GC capillary column to said supplemental detection means.

12. The GC/IR system of claim 11 in which said light pipe has an internal surface forming a passageway which is coated with a reflective gold coating for providing a chemically inert flow path and high reflectivity in the IR region.

13. The GC/IR system of claim 12 in which a first mirror is moveably positioned off-axis with respect to said first end of said light pipe tube for optimally controlling the axis of said IR energy as said IR energy is reflected from said first mirror into said first end of said light pipe tube, and in which a second mirror is moveably positioned off-axis with respect to said second end of said light pipe tube for optimally reflecting said IR energy after said IR energy is propagated through said passageway of said light pipe tube.

14. The GC/IR system of claim 13 in which said heater assembly with said floating light pipe assembly and said first and second mirrors are moveably mounted on a base plate which is adapted to drop in to substantially any commercial GC/IR sample chamber.

15. The GC/IR system of claim 11 in which said outer tube of said first transfer tube means is glass-lined steel for providing for a chemically inert flow path.

16. The GC/IR system of claim 15 in which said first transfer tube means includes an inner polyimide-coated fused silica transfer tube within said outer transfer tube for conveying said carrier gas and said peak shapes of said original sample constituents from said GC capillary column to said light pipe tube.

17. The GC/IR system of claim 16 in which said inner polyimide-coated fused silica has an inside surface which is coated with a bonded chromatographic coating to provide for chemical inertness.

18. The GC/IR system of claim 17 in which said bonded chromatographic coating is a high-temperature silicone or polymer coating.

19. The GC/IR system of claim 1 in which said second transfer tube means is retained in said second trough and extends longitudinally outward from said second trough thereby protruding beyond said heater chamber to facilitate connection of said second transfer tube means to said supplemental detection means.

20. The GC/IR system of claim 1 in which said first transfer tube means is retained in said first trough and extends longitudinally outward from said first trough thereby protruding beyond said heat chamber to facilitate connection of said first transfer tube means to said GC capillary column and to said carrier gas input means.

21. The GC/IR system of claim 11 in which said first and second fittings are gold plated for providing for a chemically inert flow path.

22. The GC/IR system of claim 5 in which said second transfer tube means includes an inner polyimide coated fused silica transfer tube.

23. The GC/IR system of claim 5 in which said second transfer tube means includes a glass-lined outer tube for providing for a chemically inert flow path.

24. The GC/IR system of claim 12 in which said first and second ends of said light pipe tube are gold plated to provide for chemica 25. The GC/IR system of claim 24 in which portions of said second transfer tube means and said outer tube of said first transfer tube means are gold plated to provide for chemical inertness.

* * * * *